United States Patent [19]
Joiner et al.

[11] Patent Number: 6,165,448
[45] Date of Patent: Dec. 26, 2000

[54] ORAL COMPOSITION WITH AN IMPROVED TEETH WHITENING EFFECT

[75] Inventors: Andrew Joiner; David William Thornthwaite, both of Bebington, United Kingdom

[73] Assignee: Chesebrough-Pond's USA Co., division of Conopco, Inc., Greenwich, Conn.

[21] Appl. No.: 09/401,879

[22] Filed: Sep. 23, 1999

[30] Foreign Application Priority Data

Sep. 25, 1998 [EP] European Pat. Off. .............. 98307835

[51] Int. Cl.$^7$ ............................... A61K 7/16; A61K 7/20
[52] U.S. Cl. .................................. 424/49; 424/49
[58] Field of Search ................................. 424/53

[56] References Cited

U.S. PATENT DOCUMENTS

| | | |
|---|---|---|
| 4,670,252 | 6/1987 | Sampathkumar . |
| 4,716,035 | 12/1987 | Sampathkumar . |
| 5,153,189 | 10/1992 | Rupp et al. . |
| 5,360,568 | 11/1994 | Madison et al. . |
| 5,360,569 | 11/1994 | Madison et al. . |
| 5,478,357 | 12/1995 | Madison et al. . |
| 5,482,515 | 1/1996 | Madison et al. . |
| 5,520,844 | 5/1996 | Venturollo et al. . |
| 5,550,256 | 8/1996 | Madison et al. . |
| 5,575,947 | 11/1996 | Venturollo et al. . |
| 5,653,910 | 8/1997 | Kerschner et al. . |
| 5,688,434 | 11/1997 | Venturollo et al. . |
| 5,785,886 | 7/1998 | Kerschner et al. . |

FOREIGN PATENT DOCUMENTS

| | | |
|---|---|---|
| 0 424 020 | 4/1991 | European Pat. Off. . |
| 95 13352 | 5/1995 | WIPO . |
| 95 13353 | 5/1995 | WIPO . |
| 95/13352 | 5/1995 | WIPO . |
| 95/13353 | 5/1995 | WIPO . |
| 96 05802 | 2/1996 | WIPO . |
| 96/05802 | 2/1996 | WIPO . |
| 96 40855 | 12/1996 | WIPO . |
| 98 23717 | 6/1998 | WIPO . |
| 98 46718 | 10/1998 | WIPO . |

*Primary Examiner*—Shep K. Rose
*Attorney, Agent, or Firm*—Milton L. Honig

[57] ABSTRACT

The present invention relates to oral care compositions with an improved teeth whitening effect. This effect is achieved by inclusion in the oral care compositions of certain organic peroxy compounds as teeth whitening/bleaching agents, particularly peroxyamidophthalamides, sulphoperbenzoic acid, monoperoxyphthalic acid, and (per)acetylatedperboric acid with imine quaternary salts as catalysts for the peroxy compounds.

6 Claims, No Drawings

ORAL COMPOSITION WITH AN IMPROVED TEETH WHITENING EFFECT

BACKGROUND OF THE INVENTION

1. Field of the Invention

The present invention relates to an oral composition with an improved teeth whitening effect. More particularly, it relates to an oral composition with an improved teeth whitening effect comprising a safe and effective amount of certain organic peroxy compounds and certain catalysts, which are capable of reacting with the organic peroxy compounds to generate more reactive oxygen species.

2. The Related Art

The use of peroxy compounds in oral care compostions has already been proposed in the prior art. Many peroxy compounds have been suggested for whitening/bleaching human teeth, and representative examples of such peroxy compounds are hydrogen peroxide, urea peroxide, organic peracids such as perphthalic acid, diperoxycarboxylic acids, 1,12-dodecanedioic peroxy acid, peroxy acetic acid and systems comprising a peroxy compound and a peroxy acid precursor which generate peroxy acetic acid in situ, such as sodium perborate and tetraacetylethylene diamine (TAED). The use of peroxy acetic acid is suggested in particular in e.g. EP-A-0545,594 (Colgate), which also sets out the various prior proposals, made in the art for several peroxy compounds as bleaching/whitening agent for human teeth.

In our WO-A-96/05802 we have described the use of various organic peroxyacids as teethwhitening agents.

SUMMARY OF THE INVENTION

We have now found that certain organic peroxy compounds, which will be defined hereinafter, when used together with certain catalysts, defined hereinafter, are much more effective than the organic peroxy compounds above, even in the absence of a peroxy acid precursor (bleach precursor), producing a teethwhitening effect much more rapidly. These certain organic peroxy compounds are selected from the group consisting of:

1) peroxy amido phthalamides having the structural formula:

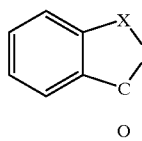
in which R = hydrogen or $C_1$–$C_4$ alkyl;
n = 1 to 5; and
X = C = O or $SO_2$ 2) sulphoperbenzoic acid ("SPB"),
3) monoperoxyphthalic acid ("MPP"), and
4) (per)acetylperoxyboric acid and/or salts thereof.

DETAILED DESCRIPTION OF THE INVENTION

The peroxy amido phthalamides of formula 1) are known per se and have been described in EP-A-325,288 and EP-A-325,289. A preferred compound of this formula is N-phthalimido hexanoic peroxy acid ("PAP") of formula 1), in which R=H, n=5 and X=C=O. An example of a compound according to formula 1) wherein X=$SO_2$ is saccharin-perhexanoic acid ("saccharin PAP"), as described in EP-A-485,927. The salts of these peroxyacids are preferably the alkalimetal salts.

The salts of sulphoperbenzoic are preferably the alkali-metal salts, particularly preferably the potassium salt ("KSPB"). This peroxyacid has been described in EP-A-124,968 and EP-A-212,913.

The salts of monoperoxyphthalic acid are preferably the alkalimetal and alkaline earth metal salts, particularly preferably the magnesium salt. The use of magnesium monoperoxyphthalate in oral care products has been described in U.S. Pat. No. 4,670,252.

(Per)acetylperoxyboric acid and salts thereof are also known per se from EP-A-212,913.

Preferably, the peroxy compound is PAP and/or KSPB.

The amount of the peroxy compounds, used in the present invention, may vary from 0.01 to 99% by weight of the oral composition, preferably from 0.1 to 30% by weight, particularly preferably from 0.1–5% by weight.

The catalysts, used in the present invention are imine quaternary salts as described in U.S. Pat. No. 5,360,568 and U.S. Pat. No. 5,360,569, which are hereby incorporated by way of Reference. Suitable examples of these imine quaternary salts are of the formula:

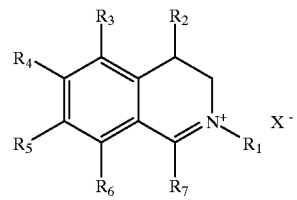

(formula I)

wherein $R_1$ is hydrogen or a $C_1$–$C_8$ alkyl group, $R_2$ is hydrogen, or a phenyl group or a keto group, $R_3$, $R_4$ and $R_5$ are hydrogen or —O-$R^1$, whereby $R^1$ is a $C_1$–$C_4$ alkyl group, $R_6$ and $R_7$ are hydrogen or a $C_1$–$C_4$ alkyl group and X is a counterion, stable in the presence of oxidizing agents, comprising $Br^-$, $BF_4^-$, $Cl^-$, $CH_3SO_4^-$, tosylate$^-$, $PF_6^-$, $F^-$, fluorophosphate cations and $C_{12}$-alkylsulphate cations.

A preferred catalyst is an imine quaternary salt of the above formula, in which $R_1$=methyl, and $R_2$–$R_6$ are all hydrogen, and X is tosylate ("Imine Quat 200").

The catalyst is used generally in an amount of 0.01 to 5% by weight, preferably 0.05 to 1.5% by weight, and particulary preferably 0.1 to 1% by weight of the oral care composition.

The oral compositions can be formulated in any suitable application form, such as gels, mouthwashes, toothpowders and toothpastes. They may be formulated into a single formulation or they may be formulated for multi compartment containers into different formulations, e.g. one containing the peroxy compound and ingredients compatible therewith, and another containing the remaining ingredients.

The oral care compositions of the present invention may furthermore comprise optional, conventional ingredients such as pharmaceutically acceptable carriers like starch, sucrose, water or water/alcohol systems etc. Small amounts of surfactants may also be included, such as anionic, nonionic and amphoteric surfactants. When formulated into a dentifrice, such formulation may contain all the usual dentifrice ingredients.

Thus, they may comprise particulate abrasive materials such as silicas, aluminas, calcium carbonates, dicalciumphosphates, calcium pyrophosphates hydroxyapatites, trimetaphosphates, insoluble hexametaphosphates, agglomerated particulate abrasive materials and so on, usually in amounts between 5 and 60% by weight.

Furthermore, the dentifrice formulations may comprise humectants such as glycerol, sorbitol, propyleneglycol, xylitol, lactitol and so on.

Binders and thickeners such as sodium carboxymethylcellulose, xanthan gum, gum arabic etc. may also be included, as well as synthetic polymers such as polyacrylates and carboxyvinyl polymers such as Carbopol®.

Flavours such as peppermint and spearmint oils may also be included, as well as preservatives, opacifying agents, colouring agents, pH-adjusting agents, sweetening agents and so on. Stabilising agents for the organic peroxy compounds such as dipicolinic acid or sodium stannate may also be usefully included.

Anti-bacterial agents may also be included such as Triclosan, chlorhexidine, copper-, zinc- and stannous salts such as zinc citrate, sodium zinc citrate and stannous pyrophosphate, sanguinarine extract, metronidazole. Further examples of anti-bacterial agents are quaternary ammonium compounds such as cetylpyridinium chloride; bis-guanides such as chlorhexidine digluconate, hexetidine, octenidine, alexidine; halogenated bisphenolic compounds such as 2,2'methylenebis-(4-chloro-6-bromophenol).

Polymeric compounds which can enhance the delivery of active ingredients such as anti-bacterial agents can also be included. Examples of such polymers are copolymers of polyvinylmethylether with maleic anhydride and other similar delivery enhancing polymers, e.g. those described in DE-A-3,942,643 (Colgate).

Furthermore anti-inflammatory agents such as ibuprofen, flurbiprofen, aspirin, indomethacin etc. may also be included.

Anti-caries agents such as sodium- and stannous fluoride, aminefluorides, monosodiumfluorophosphate, casein, plaque buffers such as urea, calcium lactate, calcium glycerophosphate, strontium polyacrylates may also be included. Other optional ingredients include vitamins such as Vitamin C, and plant extracts. Desensitising agents such as potassium citrate, potassium chloride, potasium tartrate, potassium bicarbonate, potassium oxalate, potassium nitrate as well as strontium salts may also be included.

Buffers and salts to buffer the pH and ionic strength of the compositions may also be included. The pH of the compositions usually ranges from 5–10, preferably 6–9 and especially preferably 7–8.5.

Liposomes and other encapsulates may also be used to improve delivery or stability of active ingredients.

Furthermore, the oral compositions may comprise anticalculus agents such as alkalimetal pyrophosphates, hypophosphite-containing polymers, organic phosphonates, phosphocitrates etc..

In addition, the compositions may comprise functional biomolecules such as bacteriocins, antibodies, enzymes and so on.

Other optional ingredients that may be included are e.g. effervescing systems such as sodium bicarbonate/citric acid systems, colour change systems, and so on.

Preferably, the compositions do not contain a bleach precursor.

When formulated as a mouthwash, the oral care composition usually comprises a water/alcohol solution, flavour, humectant, sweetener and colorant.

Since the peroxy compounds of the invention also have an anti-microbial property, the composition of the invention are also effective to combat plaque and caries.

The present invention will further be illustrated by way of Example.

EXAMPLE I

PAP, KSPB and acetylated sodium perborate with and without Imine Quat 200 were evaluated as to their bleaching efficacy.

The bleaching agents were evaluated as follows:

(1) Synthetic hydroxyapatite discs were polished and placed in sterile saliva at 37° C. overnight to form a pellicle.

(2) Discs were stained with tea/coffee/iron salts/saliva mixture for seven days at 37° C.

(3) Stained discs were immersed in bleaching solutions for desired time.

(4) The change in colour of the discs was measured using a Minolta chromameter CR-300 in L*a*b* mode. Using L* (initial), L* (soiled), and L* (cleaned), the percentage of stain removed was calculated.

The concentration of the PAP and the KSPB was $3.6 \times 10^{-2}$M in aqueous solution which also contained 0.5M sodium bicarbonate.

The amount of Imine Quat 200 was varied as indicated in the Table. The following results were obtained:

1) Percent stain removed with PAP ($3.6 \times 10^{-2}$M) in 0.5M NaHCO$_3$ with different concentrations of IQ200

|  | % stain removed with | | |
|---|---|---|---|
| [IQ200] (M) | 0 min | 1 min | 3 min | 5 min |
| $3.6 \times 10^{-3}$ | 0 | 67 | 86 | 91 |
| $1.8 \times 10^{-3}$ | 0 | 62 | 83 | 89 |
| $0.9 \times 10^{-3}$ | 0 | 58 | 71 | 89 |
| $3.6 \times 10^{-4}$ | 0 | 46 | 59 | 68 |
| $1.8 \times 10^{-4}$ | 0 | 40 | 69 | 76 |
| 0 | 0 | 24 | 55 | 67 |

2) Percent stain removed with potassium sulphoperbenzoic acid (KSPB) ($3.6 \times 10^{-2}$M)

|  | % stain removed with | | |
|---|---|---|---|
| Time (mins) | KSPB | KSPB/ IQ200 | NaHCO$_3$ |
| 0 | 0 | 0 | 0 |
| 0.5 | 22 | 42 | 3 |
| 1 | 34 | 55 | 3 |
| 3 | 54 | 73 | 3 |

Percent stain removed with acetylated sodium perborate (0.15% w/w) in 0.5 M sodium bicarbonate solution with IQ200 (0.1% w/w).

|  | % stain removed with | |
|---|---|---|
| Time (secs) | Acetylated sodium perborate | Acetylated sodium perborate and IQ200 |
| 0 | 0 | 0 |
| 30 | 3 | 4 |
| 60 | 16 | 22 |
| 120 | 24 | 38 |

EXAMPLE II

Bovine enamel blocks (5×5×2 mm) were attached to partial or full dentures. These were worn in the mouth for 21 days in order to build up naturally stained pellicle. The blocks were removed from the dentures and treated for 15×1 minute with one of the following mixtures:

A - 0.5 M NaHCO$_3$
B - 1% PAP/0.5M NaHCO$_3$
C - 1% PAP+0.11% Imine Quat 200/0.5M NaHCO$_3$ The colour of the bovine blocks were measured using a Minolta Chromameter CR241 in the CIE L*a*b* mode. Colour measurements were made before any treatment and after 1, 3, 5, 10 and 15 one minute treatments.

RESULTS

These are expressed in change in L* and as % stain removed.

|  | Change in L* No. of 1 min treatments | | | | |
|---|---|---|---|---|---|
| Treatment | 1 | 3 | 5 | 10 | 15 |
| A | 0.2 | 0.5 | 0.8 | 0.9 | 0.8 |
| B | 0.1 | 0.5 | 1.1 | 2.5 | 3.3 |
| C | 1.6 | 4.7 | 6.9 | 7.6 | 8.8 |
|  | % stain removed | | | | |
| A | −2 | 3 | 5 | 3 | 7 |
| B | 1 | 4 | 8 | 19 | 26 |
| C | 10 | 31 | 44 | 51 | 58 |

These results illustrate that Imine Quat catalysed peracid bleaching gives a rapid increase in L*—i.e. toothwhitening benefits after only a very short exposure.

EXAMPLE III

Example I was repeated, using different imine quaternary salts as described below. The following results were obtained:

The imine quat was modified by extending the methyl chain to butyl, hexyl and octyl, i.e.

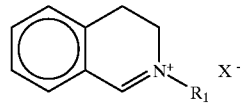

IQ200, R=methyl
IQ204, R=n-butyl
IQ206, R=n-hexyl
IQ208, R=n-octyl
X$^-$ being tosylate$^-$ and was tested in the in vitro stain model as described in Example I.

[PAP]=3.6×10$^{-3}$M, [IQ]=3.6×10$^{-3}$M in 0.5M sodium bicarbonate solution.

|  | % stain removed | |
|---|---|---|
|  | 1 min | 3 mins |
| PAP/IQ200 | 43 | 56 |
| PAP/IQ204 | 29 | 41 |
| PAP/IQ206 | 23 | 36 |
| PAP/IQ208 | 21 | 34 |
| PAP | 21 | 29 |

Repeating the experiment with PAP IQ206 gave the following results

|  | % stain removed with | |
|---|---|---|
| Time (mins) | PAP (s.d.) | PAP/IQ206 (s.d.) |
| 0 | 0 | 0 |
| 0.5 | 9 (6) | 26 (12) |
| 1.0 | 34 (5) | 48 (9) |
| 2.0 | 44 (6) | 64 (6) |

The pH profile of IQ200 catalysts was investigated, using same concentrations as above in various phosphate and borate buffers.

|  | % stain removed with | |
|---|---|---|
| PH | PAP | PAP/IQ206 |
| 6.0 | 16 | 34 |
| 7.0 | 25 | 72 |
| 8.0 | 46 | 74 |
| 9.0 | 49 | 69 |

The pH profile of IQ208 was also investigated.

|  | % stain removed with | |
|---|---|---|
| pH | PAP | PAP/IQ208 |
| 6.0 | 32 | 78 |
| 7.0 | 49 | 76 |
| 8.0 | 45 | 59 |
| 9.0 | 72 | 71 |

The ketone and 3-methyl, 3-phenyl derivatives were also evaluated under same concentrations as above.

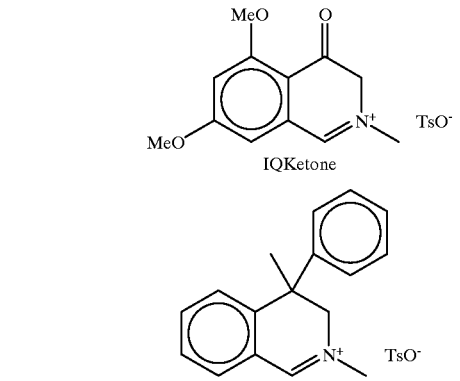

IQKetone

|  | % stain removed (s.d.) | | |
|---|---|---|---|
|  | 0.5 min | 1.0 mins | 3.0 mins |
| PAP | 3 (3) | 23 (3) | 50 (4) |
| PAP/IQ200 | 40 (5) | 68 (2) | 84 (3) |
| PAP/IQKetone | 16 (4) | 37 (5) | 69 (3) |

| | % stain removed (s.d.) | | |
|---|---|---|---|
| | 0.5 min | 1.0 mins | 3.0 mins |
| PAP/IQ200 (3-Me, 3-pH) | 17 (4) | 42 (6) | 67 (3) |

IQ200-(5,7-dimethoxy-1-methyl) gives similar results.

EXAMPLE IV

Example I was repeated using magnesium monoperoxyphthalate (H48) ($3.6 \times 10^{-2}$M) with IQ200 ($3.6 \times 10^{-3}$M)

| | % stain removed | |
|---|---|---|
| Time (mins) | H48 (s.d.) | H48 + IQ200 (s.d.) |
| 0 | 0 | 0 |
| 0.5 | 27 (5) | 89 (4) |
| 1.0 | 62 (5) | 97 (2) |
| 2.0 | 80 (6) | — |

EXAMPLE V

Bovine enamel slabs were stained with Stockey type stain and brushed with a conventional toothpaste (RDA=100), with or without PAP/IQ200 (1 %/0.11% w/w) in a brushing machine for 2,100 strokes. The increase in L* was measured with a Minolta CR241 Chromameter in the CIE L*a*b* mode hence the increase in whiteness determined.

| | $\Delta L^*$ (s.d.) |
|---|---|
| Paste (RDA = 100) | 18.3 (3.4) |
| Paste (RDA = 100) + PAP IQ200 | 23.1 (5.3) |
| | $p < 0.05$ |

What is claimed is:

1. A method for whitening teeth comprising applying to the teeth an oral composition comprising a safe and effective amount of an organic peroxy compound selected from the group consisting of:

1) peroxy amido phthalamides having the structural formula:

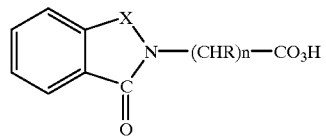

in which
R=hydrogen or $C_1$–$C_4$ alkyl;
n=1 to 5; and
x=C=O of $SO_2$ 2) sulphoperbenzoic acid;
3) monoperoxyphthalic acid; and
(per)acetylperoxyboric acid, and salts thereof, and a safe and effective amount of an imine quaternary salt of the formula

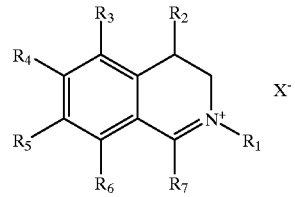

wherein $R_1$ is hydrogen or a C1–C8 alkyl group, $R_2$ is selected from the group consisting of hydrogen, a phenyl group and a keto group; $R_3$, $R_4$ and $R_5$ are hydrogen or —O-$R^1$, whereby $R^1$ is a $C_1$–$C_4$ alkyl group, $R_6$ and $R_7$ are hydrogen or a $C_1$–$C_4$ alkyl group and X is a counterion stable in the presence of oxidizing agents; and brushing the teeth with the oral composition.

2. The method according to claim 1 wherein the organic peroxy compound is N-phthalimido hexanoic peroxy acid or sulphoperbenzoic acid.

3. The method according to claim 1 wherein the imine quaternary salt is a compound wherein $R_1$ is methyl and $R_2$ to $R_6$ are all hydrogen.

4. The method according to claim 3 wherein X is a tosylate.

5. The method according to claim 1 wherein the oral composition further comprises a safe and effective amount of a fluoride compound.

6. The method according to claim 1 wherein the oral composition has a pH ranging from 7 to 8.5.

* * * * *